(12) United States Patent
Sinderby et al.

(10) Patent No.: US 8,881,725 B2
(45) Date of Patent: Nov. 11, 2014

(54) METHOD AND DEVICE FOR DETERMINING A LEVEL OF VENTILATORY ASSIST TO A PATIENT

(75) Inventors: Christer Sinderby, Toronto (CA); Jennifer Beck, Toronto (CA)

(73) Assignee: St. Michael's Hospital, Toronto, Ontario (CA)

(*) Notice: Subject to any disclaimer, the term of this patent is extended or adjusted under 35 U.S.C. 154(b) by 522 days.

(21) Appl. No.: 13/144,129

(22) PCT Filed: Jan. 14, 2010

(86) PCT No.: PCT/CA2010/000043
§ 371 (c)(1),
(2), (4) Date: Sep. 27, 2011

(87) PCT Pub. No.: WO2010/081223
PCT Pub. Date: Jul. 22, 2010

(65) Prior Publication Data
US 2012/0006327 A1      Jan. 12, 2012

Related U.S. Application Data

(60) Provisional application No. 61/193,987, filed on Jan. 15, 2009.

(51) Int. Cl.
*A61M 16/00* (2006.01)
*A62B 7/00* (2006.01)
*A61B 5/0488* (2006.01)
*A61B 5/08* (2006.01)

(52) U.S. Cl.
CPC .......... *A61M 16/0051* (2013.01); *A61B 5/0488* (2013.01); *A61M 2016/0027* (2013.01); *A61B 5/08* (2013.01)
USPC ............. 128/204.21; 128/204.23; 128/204.18

(58) Field of Classification Search
CPC ..................... A16M 16/00; A16M 2016/0021; A16M 2016/0027; A61B 5/0488; A61B 5/08
USPC ............. 128/203.14, 204.18, 204.21, 204.23, 128/204.26; 600/533, 538, 539
See application file for complete search history.

(56) References Cited

U.S. PATENT DOCUMENTS 3,890,967 A    6/1975  Elam et al.
3,961,627 A *  6/1976  Ernst et al. ............... 128/204.21

(Continued)

OTHER PUBLICATIONS

The International Search Report and Written Opinion as mailed on Apr. 13, 2010 for International Application No. PCT/CA2010/000043.

(Continued)

*Primary Examiner* — Justine Yu
*Assistant Examiner* — Douglas Sul

(57) ABSTRACT

A method and device determine a level of mechanical ventilatory assist to be delivered to a patient. A patient's neural respiratory drive is measured and multiplied by an existing amplification factor to obtain an existing predicted ventilatory pressure. A mechanical ventilator is controlled accordingly. An existing resulting pressure is measured. The patient's neural respiratory drive is multiplied by a modified amplification factor to obtain a new predicted pressure. The existing and new predicted pressures are compared to determine an anticipated change in pressure. The mechanical ventilator is now controlled according to the new predicted pressure. A new resulting pressure is measured. The existing and new resulting pressures are compared to determine an actual change in pressure. The anticipated and actual changes in pressure are compared. The amplification factor is increased, maintained or decreased in response to the comparison between the anticipated and actual changes in pressure.

18 Claims, 2 Drawing Sheets

(56) References Cited

U.S. PATENT DOCUMENTS

| | | | |
|---|---|---|---|
| 5,671,752 | A | 9/1997 | Sinderby et al. |
| 5,820,560 | A * | 10/1998 | Sinderby et al. ............... 600/546 |
| 6,609,517 | B1 * | 8/2003 | Estes et al. ............... 128/204.23 |
| 6,668,824 | B1 * | 12/2003 | Isaza et al. ............... 128/202.22 |
| 6,739,336 | B1 * | 5/2004 | Jalde et al. ............... 128/204.21 |
| 7,021,310 | B1 | 4/2006 | Sinderby et al. |
| 2003/0226565 | A1 | 12/2003 | Sinderby et al. |
| 2009/0159082 | A1 | 6/2009 | Eger |

OTHER PUBLICATIONS

Brander, L., et al., "Titration and Implementation of Neurally Adjusted Ventilatory Assist in Critically Ill Patients," PubMed, U.S. National Library of Medicine and the National Institutes of Health, Jan. 14, 2009, (Web Article).

* cited by examiner

METHOD AND DEVICE FOR DETERMINING A LEVEL OF VENTILATORY ASSIST TO A PATIENT

CROSS-REFERENCE TO RELATED APPLICATIONS

The present application claims the benefit of U.S. Provisional Application No. 61/193,987, filed Jan. 15, 2009, and is a U.S. national phase of PCT International Application No. PCT/CA2010/000043, filed on Jan. 14, 2010, both applications are incorporated herein by reference.

FIELD

The present invention is concerned with determining a level of ventilatory assist to be delivered a patient.

BACKGROUND

In practice, an adequate level of ventilatory assist to be delivered to a patient under mechanical ventilation is difficult to determine since unloading of the patient involves compensation for increased respiratory demand in terms of metabolic drive, resistive and elastic loads imposed by the patient's respiratory system, as well as weakness of the inspiratory muscles. There is therefore a need for a technique that facilitates such determination.

SUMMARY

The present invention relates to a method for determining a level of ventilatory assist to be delivered to a patient by a mechanical ventilator in response to a measure of a patient's neural respiratory drive multiplied by an amplification factor, comprising: calculating an existing predicted ventilatory assist pressure; measuring an existing resulting pressure delivered to the patient by the mechanical ventilator; changing the amplification factor from an existing amplification factor to a new amplification factor; calculating a new predicted ventilatory assist pressure using the new amplification factor; measuring a new resulting pressure delivered to the patient by the mechanical ventilator after the amplification factor has been changed from the existing amplification factor to the new amplification factor; comparing the new predicted ventilatory assist pressure and the existing predicted ventilatory assist pressure to determine an anticipated change in pressure that will be delivered to the patient by the mechanical ventilator; comparing the new resulting pressure and the existing resulting pressure to determine an actual change in pressure delivered to the patient by the mechanical ventilator; comparing the anticipated change in pressure with the actual change in pressure; and delivering a decision to increase, maintain or decrease the amplification factor in response to the comparison between the anticipated change and the actual change in pressure.

The present invention is also concerned with a device for determining a level of ventilatory assist to be delivered to a patient by a mechanical ventilator in response to a measure of a patient's neural respiratory drive multiplied by an amplification factor, comprising: a first calculator of an existing predicted ventilatory assist pressure; a first sensor of an existing resulting pressure delivered to the patient by the mechanical ventilator; a modifier of the amplification factor from an existing amplification factor to a new amplification factor; a second calculator of a new predicted ventilatory assist pressure using the new amplification factor; a second sensor of a new resulting pressure delivered to the patient by the mechanical ventilator after the amplification factor has been changed from the existing amplification factor to the new amplification factor; a first comparator of the new predicted ventilatory assist pressure and the existing predicted ventilatory assist pressure to determine an anticipated change in pressure that will be delivered to the patient by the mechanical ventilator; a second comparator of the new resulting pressure and the existing resulting pressure to determine an actual change in pressure delivered to the patient by the mechanical ventilator; a third comparator of the anticipated change in pressure and the actual change in pressure; and a third calculator of a decision to increase, maintain or decrease the amplification factor in response to the comparison between the anticipated change and the actual change in pressure.

BRIEF DESCRIPTION OF THE DRAWINGS

The foregoing and other features of the method and device for determining a level of ventilatory assist will become more apparent from reading of the following non restrictive description of illustrative embodiments thereof, given by way of example only with reference to the accompanying drawings in which.

DETAILED DESCRIPTION

Figure 1:
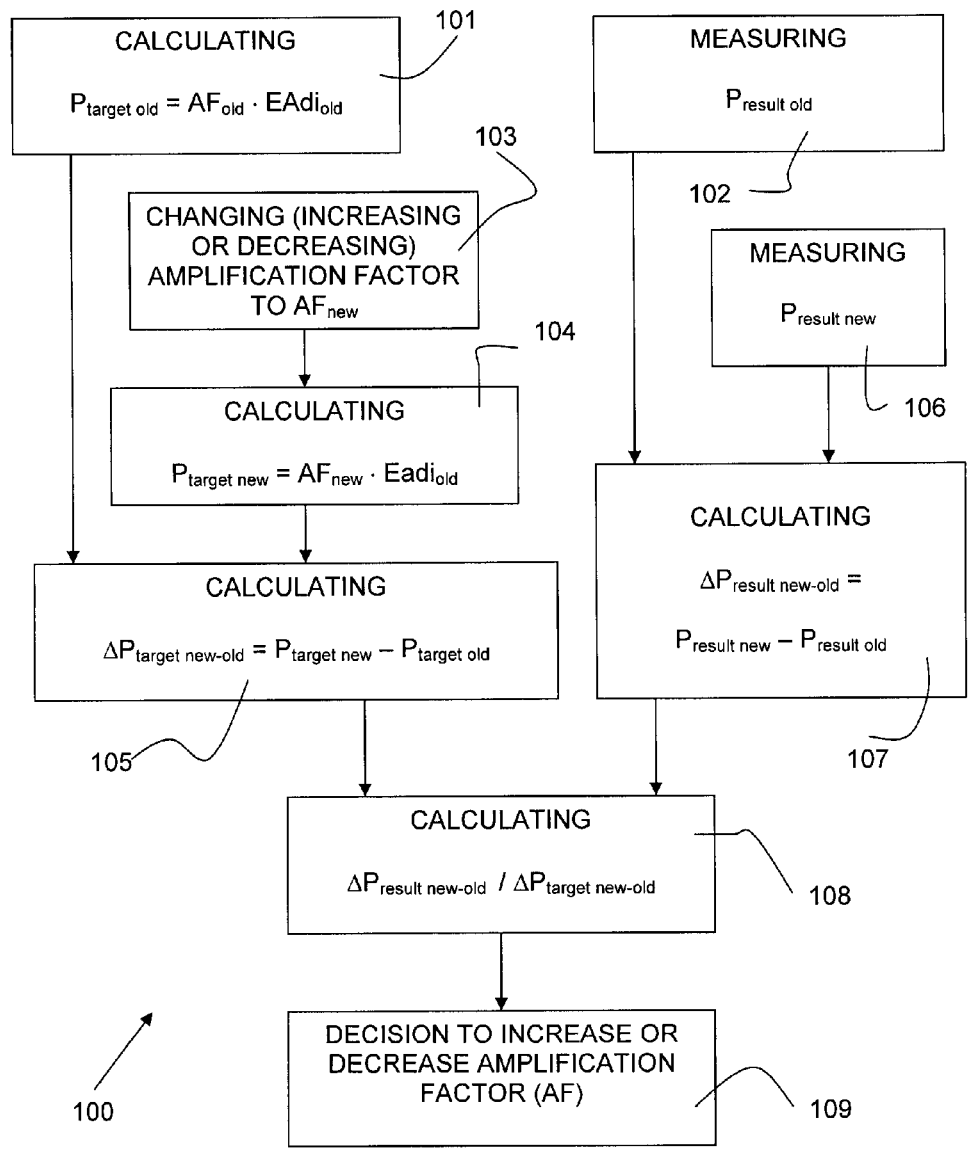
FIG. 1 is a schematic flow chart of a method for determining the level of ventilatory assist to be delivered to the patient by the mechanical ventilator in response to the measure of the patient's neural respiratory drive multiplied by the amplification factor.

The method and device for determining the level of ventilatory assist to be delivered to the patient by the mechanical ventilator in response to the measure of the patient's neural respiratory drive multiplied by the amplification factor will now be described.

The level of ventilatory assist to the patient may be controlled by applying to the mechanical ventilator a control signal representative of a predicted ventilatory assist pressure $P_{target}$ determined as a function of the patient's neural respiratory drive and an amplification factor AF. For example, the electrical activity of the patient's diaphragm EAdi may be measured as the patient's neural respiratory drive and may be multiplied by the amplification factor AF to describe the predicted ventilatory assist pressure $P_{target}$.

An example of technique for measuring the electrical activity of the patient's diaphragm EAdi is described in U.S. Pat. No. 5,671,752 (Sinderby et al.) issued on Sep. 30, 1997. Although in the herein described embodiment the electrical activity of the patient's diaphragm EAdi is used as a representation of the patient's neural respiratory drive, it should be kept in mind that any other signal, for example the electrical activity of another respiratory related muscle can be used as the representation of the patient's neural respiratory drive.

The method and device for determining the level of ventilatory assist to be delivered to the patient uses a prediction (predicted ventilatory assist pressure $P_{target}$) of the pressure to be delivered to the patient by the mechanical ventilator in response to a given change of the amplification factor AF and a comparison between the predicted ventilatory assist pressure $P_{target}$ and a resulting pressure $P_{result}$ actually delivered to the patient by the mechanical ventilator in response to the given change of the amplification factor AF. For example, if the measured electrical activity of the patient's diaphragm EAdi is 10 µV and the amplification factor AF is increased from 0 cm $H_2O/\mu V$ to 1 cm $H_2O/\mu V$, it can be expected that the predicted ventilatory assist pressure $P_{target}$ will be 10 cm $H_2O$. If the resulting pressure $P_{result}$ turns out to be 10 cm $H_2O$, this means that the patient has absorbed/accepted the whole ventilatory assist with no reduction of the patient's neural respiratory drive since the electrical activity of the patient's diaphragm EAdi remained unchanged. If, on the other hand, the electrical activity of the patient's diaphragm EAdi reduced from 10 µV to 1 µV, the resulting pressure $P_{result}$ becomes 1 cm $H_2O$ although the predicted ventilatory assist pressure $P_{target}$ was 10 cm $H_2O$, showing that the patient does not require the increase of ventilatory assist and rather down regulates his/her neural respiratory drive (EAdi).

If the patient already receives ventilatory assist and, for example, the amplification factor AF is 1 and the electrical activity of the patient's diaphragm EAdi is 10 µV, it is possible to calculate an expected increase of the predicted pressure $P_{target}$ if, for example, the amplification factor AF is increased to 1.5. The predicted ventilatory assist pressure will then be $P_{target}$=1.5 cm $H_2O/\mu V \times 10$ µV=15 cm $H_2O$. If the increase of the amplification factor AF from 1.0 cm $H_2O/\mu V$ to 1.5 cm $H_2O/\mu V$ increases the resulting pressure $P_{result}$ from 10 cm $H_2O$ to 15 cm $H_2O$, this indicates that the patient welcome the increase of ventilatory assist (increase in pressure) and maintains his/her neural respiratory drive (EAdi).

If, on the other hand, the amplification factor AF is increased from 1.0 cm $H_2O/\mu V$ to 1.5 cm $H_2O/\mu V$ but the resulting pressure $P_{result}$ increases from 10 cm $H_2O$ to 12 cm $H_2O$ while the predicted ventilatory assist pressure $P_{target}$ indicates a 5 cm $H_2O$ increase, the patient does not welcome the whole increase in ventilatory assist and rather down regulates his/her neural respiratory drive (EAdi).

The method 100 and device 200 for determining the level of ventilatory assist to be delivered to the patient by the mechanical ventilator in response to the measure of a patient's neural respiratory drive multiplied by the amplification factor will now be described with reference to FIGS. 1 and 2.

Figure 2:
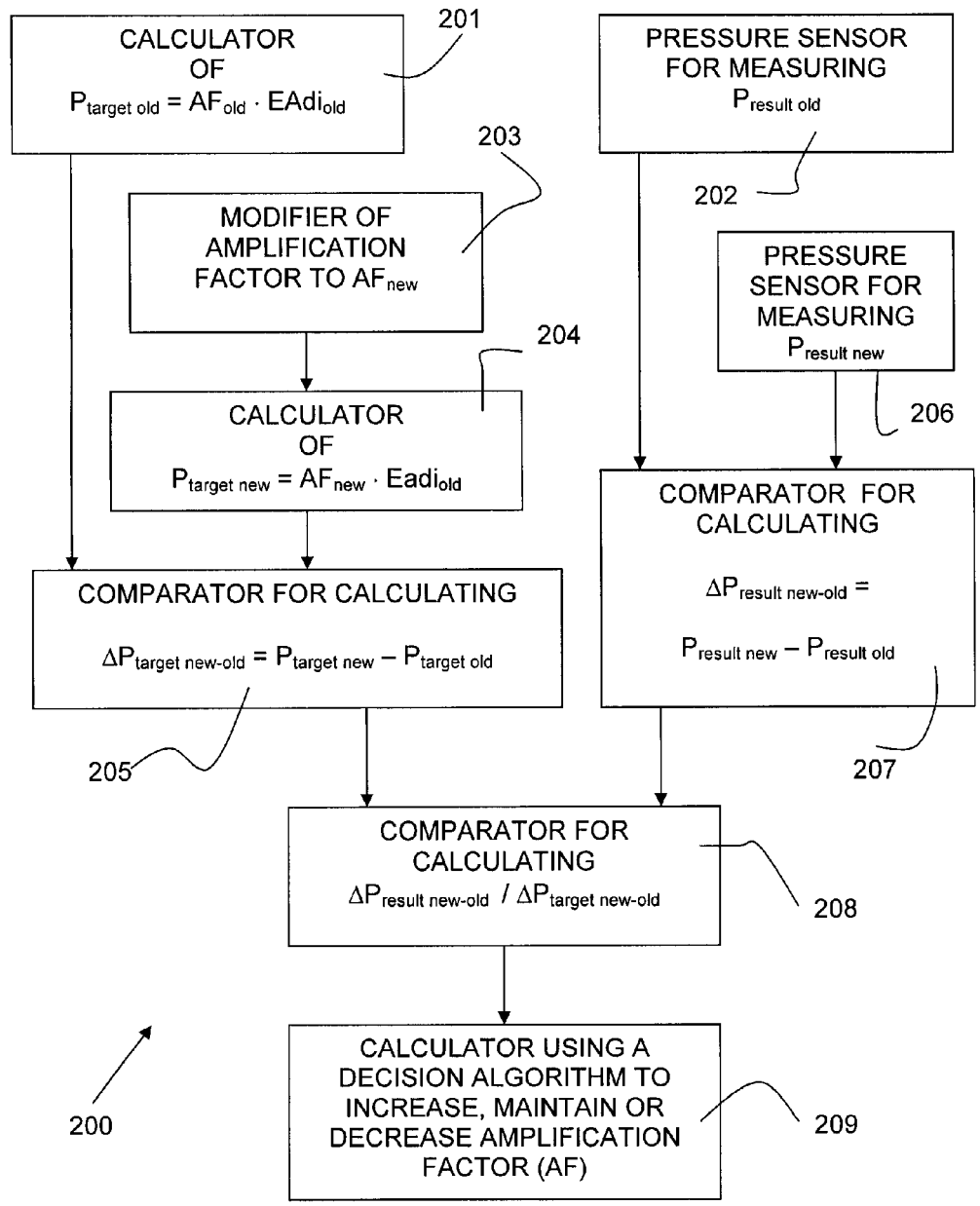
FIG. 2 is a schematic block diagram of a device for determining the level of ventilatory assist to be delivered to the patient by the mechanical ventilator in response to the measure of the patient's neural respiratory drive multiplied by the amplification factor.

Operation 101 (FIG. 1)

At a stable level of ventilatory assist, a calculator 201 (FIG. 2) calculates an existing predicted ventilatory assist pressure $P_{target\ old}$ by multiplying the existing amplification factor $AF_{old}$ by the existing electrical activity of the patient's diaphragm $EAdi_{old}$, in accordance with the following relation:

$$P_{target\ old}=AF_{old} \cdot EAdi_{old} \quad (1)$$

Operation 102 (FIG. 1)

At a stable level of ventilatory assist, a pressure sensor 202 (FIG. 2) measures the existing resulting pressure $P_{result\ old}$ delivered to the patient by the mechanical ventilator. This can be made, for example, by measuring the pressure in the mechanical ventilator or mechanical ventilator circuit.

When the neurally controlled ventilator system has been operated at a given amplification factor for a certain time, the existing predicted pressure $P_{target\ old}$ and the existing resulting pressure $P_{result\ old}$ will assume very similar if not the same values.

Operation 103 (FIG. 1)

A modifier 203 (FIG. 2) of amplification factor, for example a keyboard, is used by the medical personnel, for example a caregiver, to change (increase or decrease) an existing amplification factor $AF_{old}$ to a new amplification factor $AF_{new}$.

Alternatively, the modifier 203 can be implemented by an automatic computerized modifier requiring no intervention from the medical personnel.

Operation 104 (FIG. 1)

A calculator 204 (FIG. 2) calculates a new predicted ventilatory assist pressure $P_{target\ new}$ by multiplying the new amplification factor $AF_{new}$ by the existing electrical activity of the patient's diaphragm $EAdi_{old}$, in accordance with the following relation:

$$P_{target\ new}=AF_{new} \cdot EAdi_{old} \quad (2)$$

Operation 105 (FIG. 1)

A comparator 205 (FIG. 2) compares the new predicted ventilatory assist pressure $P_{target\ new}$ to the existing predicted ventilatory assist pressure $P_{target\ old}$ using, for example, the following relation:

$$\Delta P_{target\ new-old}=P_{target\ new}-P_{target\ old} \quad (3)$$

to show an anticipated change (increase or decrease) in pressure ($\Delta P_{target\ new-old}$) that will be delivered to the patient by the mechanical ventilator.

Operation 106 (FIG. 1)

A pressure sensor 206 (FIG. 2) measures the new resulting pressure $P_{result\ new}$ actually delivered to the patient by the mechanical ventilator following change from the existing amplification factor $AF_{old}$ to the new amplification factor $AF_{new}$. This can be made, for example, by measuring the pressure in the mechanical ventilator or mechanical ventilator circuit.

Operation 107 (FIG. 1)

A comparator 207 (FIG. 2) compares the new resulting pressure $P_{result\ new}$ to the existing resulting pressure $P_{result\ old}$ using, for example, the following relation:

$$\Delta P_{result\ new-old}=P_{result\ new}-P_{result\ old} \quad (4)$$

to show an actual change (increase or decrease) in pressure ($\Delta P_{result\ new-old}$) delivered to the patient by the mechanical ventilator.

Operation 108 (FIG. 1)

A comparator 208 (FIG. 2) compares the anticipated change (increase or decrease) in pressure $\Delta P_{target\ new-old}$ to the actual change (respectively increase or decrease) in pressure $\Delta P_{result\ new-old}$ using, for example, calculation of the following ratio:

$$\Delta P_{result\ new-old}/\Delta P_{target\ new-old} \quad (5)$$

to express a relation between the anticipated change and actual change in the level of pressure delivered to the patient by the mechanical ventilator. The ratio $\Delta P_{result\ new-old}/\Delta P_{target\ new-old}$ will range between 0 and 1, such that the response to change (increase or decrease) of the amplification factor AF can be divided into classes as described hereinafter.

When the amplification factor is increased in operation 103 (FIG. 1), a ratio $\Delta P_{result\ new-old}/\Delta P_{target\ new-old}$ equal to 1 suggests that the increase in ventilatory assist from the mechanical ventilator was welcomed by the patient, whereas a ratio $\Delta P_{result\ new-old}/\Delta P_{target\ new-old}$ of 0.5 suggests that only 50% of the increase in ventilatory assist delivered by the mechanical ventilator was welcomed by the patient and that the patient down regulated his/her neural respiratory drive (EAdi).

Operation 109 (FIG. 1)

A calculator 209 (FIG. 2) includes a decision algorithm implemented to take a decision as to increase or decrease the amplification factor AF for example as described hereinafter.

When the amplification factor AF is increased in operation 103 (FIG. 1), the ratio $\Delta P_{result\ new-old}/\Delta P_{target\ new-old}$ is positive. For example, the decision can then be as follows:

In response to a ratio $\Delta P_{result\ new\text{-}old}/\Delta P_{target\ new\text{-}old}=0.8$ to 1, the decision algorithm of the calculator 209 (FIG. 2) delivers a decision to further increase the amplification factor AF;

In response to a ratio $\Delta P_{result\ new\text{-}old}/\Delta P_{target\ new\text{-}old}=0.5$ to 0.8, the decision algorithm of the calculator 209 (FIG. 2) delivers a decision to maintain the amplification factor AF unchanged; and In response to a ratio $\Delta P_{result\ new\text{-}old}/\Delta P_{target\ new\text{-}old}<0.5$, the decision algorithm of the calculator 209 (FIG. 1) delivers a decision to decrease the amplification factor AF.

When the amplification factor AF is decreased in operation 103 (FIG. 1), the ratio $\Delta P_{result\ new\text{-}old}/\Delta P_{target\ new\text{-}old}$ is negative. For example, the decision can then be as follows:

In response to a ratio $\Delta P_{result\ new\text{-}old}/\Delta P_{target\ new\text{-}old}=-0.8$ to $-1$, the decision algorithm of the calculator 209 (FIG. 2) delivers a decision to increase the amplification factor AF;

In response to a ratio $\Delta P_{result\ new\text{-}old}/\Delta P_{target\ new\text{-}old}=-0.5$ to $-0.8$, the decision algorithm of the calculator 209 (FIG. 2) delivers a decision to maintain the amplification factor AF unchanged; and In response to a ratio $\Delta P_{result\ new\text{-}old}/\Delta P_{target\ new\text{-}old}>-0.5$, the decision algorithm of the calculator 209 (FIG. 2) delivers a decision to further decrease the amplification factor AF.

If the decision algorithm of the calculator 209 (FIG. 2) requests a change (increase or decrease) of the amplification factor, the complete, above described procedure including operations 101-109 is then repeated.

In operation 103 (FIG. 1), the modifier 203 (FIG. 2) of amplification factor will be used by the medical personnel to change (increase or decrease) or automatically changes (increase or decrease) the amplification factor AF as indicated. As a non limitative example, the modifier 203 (FIG. 2) may be designed to automatically change the amplification factor AF as a function of the ratio $\Delta P_{result\ new\text{-}old}/\Delta P_{target\ new\text{-}old}$ according to a predetermined relation, for example by predetermined steps. Alternatively, it can be left to the medical personnel to decide to what extent the amplification factor should be changed through the modifier 203 (FIG. 2).

The calculator 201, calculator 204, comparator 205, comparator 207, comparator 208 and calculator 209 can be implemented by a computer or computers, for example a single, suitably programmed general purpose computer.

What is claimed is:

1. A method for determining a level of ventilatory assist to be delivered to a patient by a mechanical ventilator, comprising:
   measuring a patient's neural respiratory drive;
   using a first calculator to multiply the patient's neural respiratory drive by an existing value of an amplification factor to obtain an existing predicted ventilatory assist pressure;
   applying to the mechanical ventilator a first control signal representative of the existing predicted ventilatory assist pressure;
   measuring an existing resulting pressure delivered to the patient by the mechanical ventilator as a result of the first control signal;
   using a modifier to increase or decrease the amplification factor to obtain a new value of the amplification factor;
   using a second calculator to multiply the patient's neural respiratory drive by the new value of the amplification factor to obtain a new predicted ventilatory assist pressure;
   applying to the mechanical ventilator a second control signal representative of the new predicted ventilatory assist pressure;
   measuring a new resulting pressure delivered to the patient by the mechanical ventilator as a result of the second control signal;
   using a first comparator to compare the new predicted ventilatory assist pressure and the existing predicted ventilatory assist pressure to determine an anticipated change in pressure that will be delivered to the patient by the mechanical ventilator;
   using a second comparator to compare the new resulting pressure and the existing resulting pressure to determine an actual change in pressure delivered to the patient by the mechanical ventilator;
   using a third comparator to compare the anticipated change in pressure with the actual change in pressure; and
   using a third calculator to deliver a decision to increase, maintain or decrease the amplification factor in response to the comparison between the anticipated change and the actual change in pressure.

2. A method for determining a level of ventilatory assist as defined in claim 1, wherein measuring the existing resulting pressure comprises measuring a pressure in patient's airways.

3. A method for determining a level of ventilatory assist as defined in claim 1, wherein comparing the new predicted ventilatory assist pressure $P_{target\ new}$ and the existing predicted ventilatory assist pressure $P_{target\ old}$ comprises using the following relation:

$$\Delta P_{target\ new\text{-}old} = P_{target\ new} - P_{target\ old}$$

to show an anticipated change in pressure $\Delta P_{target\ new\text{-}old}$ that will be delivered to the patient by the mechanical ventilator.

4. A method for determining a level of ventilatory assist as defined in claim 3, wherein:
   comparing the new resulting pressure $P_{result\ new}$ and the existing resulting pressure $P_{result\ old}$ comprises using the following relation:

$$\Delta P_{result\ new\text{-}old} = P_{result\ new} - P_{result\ old}$$

to show an actual change in pressure $\Delta P_{result\ new\text{-}old}$ delivered to the patient by the mechanical ventilator; and
   comparing the anticipated change in pressure $\Delta P_{target\ new\text{-}old}$ to the actual change in pressure $\Delta P_{result\ new\text{-}old}$ comprises calculating a ratio:

$$\Delta P_{result\ new\text{-}old}/\Delta P_{target\ new\text{-}old}$$

to express a relation between the anticipated change and actual change in the level of pressure delivered to the patient by the mechanical ventilator.

5. A method for determining a level of ventilatory assist as defined in claim 4, wherein:
   the amplification factor is increased;
   the ratio $\Delta P_{result\ new\text{-}old}/\Delta P_{target\ new\text{-}old}$ is positive;
   delivering a decision comprises:
      in response to the ratio $\Delta P_{result\ new\text{-}old}/\Delta P_{target\ new\text{-}old}$ situated in an upper range, delivering a decision to further increase the amplification factor;
      in response to the ratio $\Delta P_{result\ new\text{-}old}/\Delta P_{target\ new\text{-}old}$ situated in a middle range, delivering a decision to maintain the amplification factor unchanged; and
      in response to the ratio $\Delta P_{result\ new\text{-}old}/\Delta P_{target\ new\text{-}old}$ situated in a lower range, delivering a decision to decrease the amplification factor.

6. A method for determining a level of ventilatory assist as defined in claim 4, wherein:

the amplification factor is decreased;
the ratio $\Delta P_{result\ new-old}/\Delta P_{target\ new-old}$ is negative;
delivering a decision comprises:
in response to a ratio $\Delta P_{result\ new-old}/\Delta P_{target\ new-old}$ situated in a lower range, delivering a decision to increase the amplification factor;
in response to a ratio $\Delta P_{result\ new-old}/\Delta P_{target\ new-old}$ situated in a middle range, delivering a decision to maintain the amplification factor unchanged; and
in response to a ratio $\Delta P_{result\ new-old}/\Delta P_{target\ new-old}$ situated in an upper range, delivering a decision to further decrease the amplification factor.

7. A method for determining a level of ventilatory assist as defined in claim 1, wherein measuring the new resulting pressure comprises measuring a pressure in patient's airways.

8. A method for determining a level of ventilatory assist as defined in claim 1, wherein comparing the new resulting pressure $P_{result\ new}$ and the existing resulting pressure $P_{result\ old}$ comprises using the following relation:

$$\Delta P_{result\ new-old} = P_{result\ new} - P_{result\ old}$$

to show an actual change in pressure $\Delta P_{result\ new-old}$ delivered to the patient by the mechanical ventilator.

9. A method for determining a level of ventilatory assist as defined in claim 1, wherein the patient's neural respiratory drive is represented by the electrical activity of the patient's diaphragm.

10. A device for determining a level of ventilatory assist to be delivered to a patient by a mechanical ventilator, comprising:
means for measuring a patient's neural respiratory drive;
a first calculator for multiplying the patient's neural respiratory drive by an existing value of an amplification factor to obtain an existing predicted ventilatory assist pressure used as a first control signal applied to the mechanical ventilator;
a sensor of an existing resulting pressure delivered to the patient by the mechanical ventilator as a result of the first control signal;
a modifier of the amplification factor configured to provide a new value of the amplification factor;
a second calculator for multiplying the patient's neural respiratory drive by the new value of the amplification factor to obtain a new predicted ventilatory assist pressure used as a second control signal applied to the mechanical ventilator;
a sensor of a new resulting pressure delivered to the patient by the mechanical ventilator as a result of the second control signal;
a first comparator of the new predicted ventilatory assist pressure and the existing predicted ventilatory assist pressure to determine an anticipated change in pressure that will be delivered to the patient by the mechanical ventilator
a second comparator of the new resulting pressure and the existing resulting pressure to determine an actual change in pressure delivered to the patient by the mechanical ventilator;
a third comparator of the anticipated change in pressure and the actual change in pressure; and
a third calculator of a decision to increase, maintain or decrease the amplification factor in response to the comparison between the anticipated change and the actual change in pressure.

11. A device for determining a level of ventilatory assist as defined in claim 10, wherein the sensor of the existing resulting pressure comprises a sensor of a pressure in patient's airways.

12. A device for determining a level of ventilatory assist as defined in claim 10, wherein the first comparator of the new predicted ventilatory assist pressure $P_{target\ new}$ and the existing predicted ventilatory assist pressure $P_{target\ old}$ uses the following relation:

$$\Delta P_{target\ new-old} = P_{target\ new} - P_{target\ old}$$

to show an anticipated change in pressure $\Delta P_{target\ new-old}$ that will be delivered to the patient by the mechanical ventilator.

13. A device for determining a level of ventilatory assist as defined in claim 12, wherein:
the second comparator of the new resulting pressure $P_{result\ new}$ and the existing resulting pressure $P_{result\ old}$ uses the following relation:

$$\Delta P_{result\ new-old} = P_{result\ new} - P_{result\ old}$$

to show an actual change in pressure $\Delta P_{result\ new-old}$ delivered to the patient by the mechanical ventilator; and
the third comparator of the anticipated change in pressure $\Delta P_{target\ new-old}$ to the actual change in pressure $\Delta P_{result\ new-old}$ calculates a ratio:

$$\Delta P_{result\ new-old}/\Delta P_{target\ new-old}$$

to express a relation between the anticipated change and actual change in the level of pressure delivered to the patient by the mechanical ventilator.

14. A device for determining a level of ventilatory assist as defined in claim 13, wherein:
the modifier is configured to increase or decrease the amplification factor so that, when the amplification factor is increased, the ratio $\Delta P_{result\ new-old}/\Delta P_{target\ new-old}$ is positive; and
the third calculator is configured to deliver, when the ratio $\Delta P_{result\ new-old}/\Delta P_{target\ new-old}$ is positive:
a decision to further increase the amplification factor in response to the ratio $\Delta P_{result\ new-old}/\Delta P_{target\ new-old}$ situated in an upper range;
a decision to maintain the amplification factor unchanged in response to the ratio $\Delta P_{result\ new-old}/\Delta P_{target\ new-old}$ situated in a middle range; and
a decision to decrease the amplification factor in response to the ratio $\Delta P_{result\ new-old}/\Delta P_{target\ new-old}$ situated in a lower range.

15. A device for determining a level of ventilatory assist as defined in claim 13, wherein:
the modifier is configured to increase or decrease the amplification factor so that, when the amplification factor is decreased, the ratio $\Delta P_{result\ new-old}/\Delta P_{target\ new-old}$ is negative; and
the third calculator is configured to deliver, when the ratio $\Delta P_{result\ new-old}/\Delta P_{target\ new-old}$ is negative:
a decision to increase the amplification factor in response to a ratio $\Delta P_{result\ new-old}/\Delta P_{target\ new-old}$ situated in a lower range;
a decision to maintain the amplification factor unchanged in response to a ratio $\Delta P_{result\ new-old}/\Delta P_{target\ new-old}$ situated in a middle range; and
a decision to further decrease the amplification factor in response to a ratio $\Delta P_{result\ new-old}/\Delta P_{target\ new-old}$ situated in an upper range.

16. A device for determining a level of ventilatory assist as defined in claim 10, wherein the sensor of the new resulting pressure comprises a sensor of a pressure in patient's airways.

17. A device for determining a level of ventilatory assist as defined in claim 10, wherein the second comparator of the new resulting pressure $P_{result\ new}$ and the existing resulting pressure $P_{result\ old}$ uses the following relation:

$$\Delta P_{result\ new\text{-}old} = P_{result\ new} - P_{result\ old}$$

to show an actual change in pressure $\Delta P_{result\ new\text{-}old}$ delivered to the patient by the mechanical ventilator.

18. A device for determining a level of ventilatory assist as defined in claim 10, wherein the patient's neural respiratory drive is represented by the electrical activity of the patient's diaphragm.

\* \* \* \* \*